United States Patent [19]
Cahill et al.

[11] Patent Number: 4,953,573
[45] Date of Patent: Sep. 4, 1990

[54] ROD MONITORING DEVICE

[75] Inventors: Michael J. Cahill; John Dawson, both of Coventry, England

[73] Assignee: Molins plc, Milton Keynes, England

[21] Appl. No.: 369,756

[22] Filed: Jun. 23, 1989

[30] Foreign Application Priority Data

Jun. 23, 1988 [GB] United Kingdom ............... 8814929

[51] Int. Cl.$^5$ ............................................... A24C 5/32
[52] U.S. Cl. ..................................... 131/280; 131/904; 131/908; 73/861.18; 209/537
[58] Field of Search ............... 131/280, 904, 908, 910, 131/84.1, 906; 73/861.18, 861.21; 209/537

[56] References Cited

U.S. PATENT DOCUMENTS 4,685,475 8/1987 Ridler et al. ................... 131/280

Primary Examiner—V. Millin
Assistant Examiner—J. L. Doyle
Attorney, Agent, or Firm—Antonelli, Terry, Stout & Kraus

[57] ABSTRACT

A sensor for detecting open longitudinal seams in the continuous wrapper of cigarette or cigarette filter rod produced by a continuous rod-making machine relies on detection by a microphone (54) of disturbance caused by the defective seam to an air stream. The air stream is generated from a narrow slot (44) and normally follows a fixed, preferably flat, surface (40) closely adjacent to the longitudinal path of a rod (12). The surface (40) is part of a body (22) which contains the microphone (54) and connecting leads (56, 58), together with a passage (36) allowing sound to reach the microphone. Air is bled through a small bore (52) and through a further bore (30) containing a sound-insulating filter (66) to provide a purging air flow in the passage (36).

14 Claims, 1 Drawing Sheet

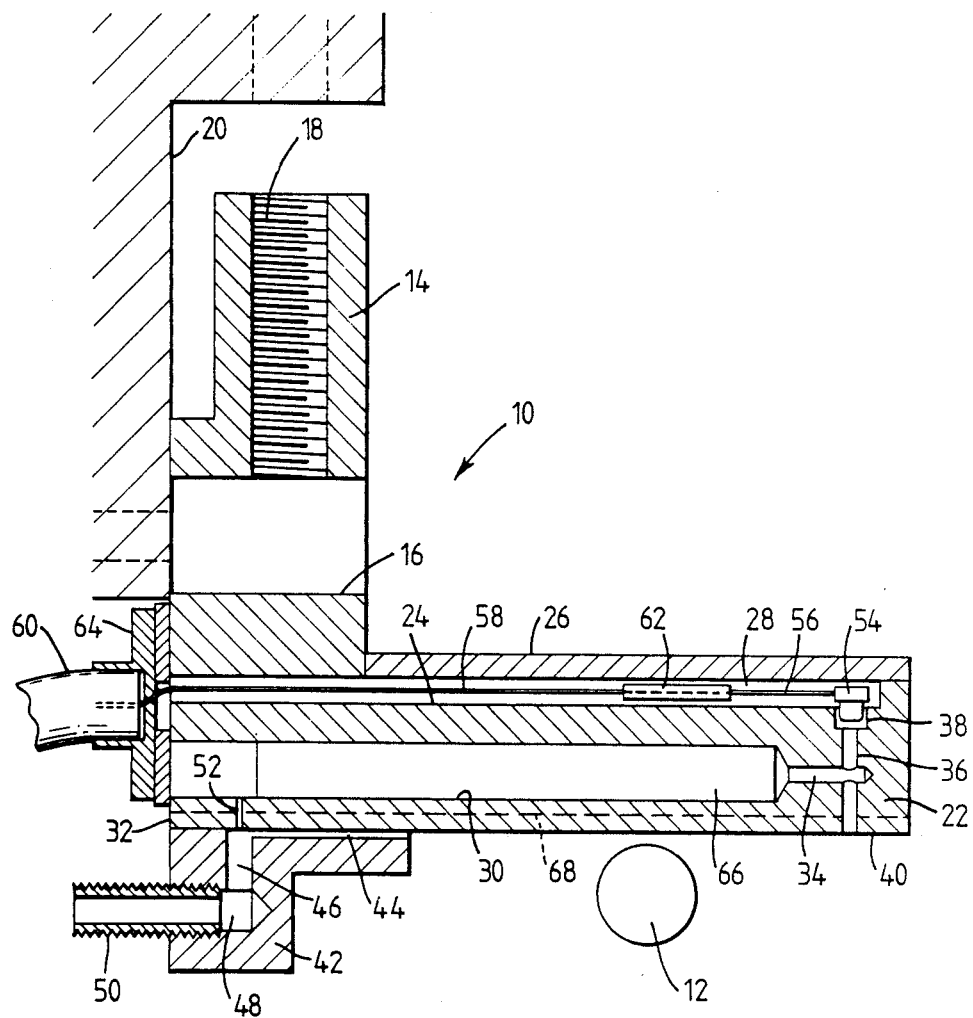

ROD MONITORING DEVICE

BACKGROUND OF THE INVENTION

This invention relates to monitoring cigarette or cigarette filter rod while it is moving in an axial direction, particularly for detection of an open or otherwise imperfect longitudinal seam in a wrapper for the rod.

U.S. Pat. No. 4685475 discloses a cigarette or cigarette filter rod monitoring device in which a stream of air is directed at the rod while it is moving axially and in which a microphone is used to monitor sound caused by the air stream after it has passed in Coanda effect contact with the rod. In particular a seam defect is said to disrupt the air stream to cause a measurable change in the monitored sound. This prior art device has a channel through which the rod passes, a passage communicating with the channel for directing an air stream tangentially at the rod, and a duct also communicating with the channel and additionally with a microphone. The passage through which the rod passes closely surrounds the rod and this can cause potential contamination problems, particularly due to tobacco dust and particles accumulating in the duct. Also, since the device relies on Coanda effect contact of an air stream with the rod it is particularly sensitive to the position of the rod. Probably in view of this the device is located at the end of the garniture where the rod position is reasonably well defined but even there in practice the minor variations in rod position as it passes through the garniture can cause monitoring difficulties. A further disadvantage of the prior art device is that its location at the end of the garniture tends to impede operators during a rod break-in.

SUMMARY OF THE INVENTION

It is an object of the present invention to provide a rod monitoring device which avoids at least some of the disadvantages of the prior art device.

Accordingly, the invention provides a monitoring device, particularly for detecting imperfect longitudinal seams in the wrapper of a cigarette or cigarette filter rod, comprising a fixed surface which may be located adjacent to an axial path of the rod, means for directing an air stream along said surface in a direction generally transverse to said path, and means for monitoring sound caused by said stream after it has passed adjacent said path, whereby disturbance of said stream caused by defects in a rod on said path may be detected by said monitoring means.

Preferably the directing means and the fixed surface are arranged so that the air stream flows in Coanda effect contact with said surface. Preferably the fixed surface is flat. The directing means may comprise a nozzle in the form of a slit one side of which is defined by said surface.

The sound monitoring means may comprise a microphone, which may be located in a passage having an opening in said surface. An air flow may be established in said passage to eliminate or reduce contamination by tobacco particles. Means may be provided for insulating the microphone from sound which may be caused in generating said air flow in said passage.

Preferably the fixed surface is arranged so that the periphery of a rod on said path is spaced from said surface by a minimum distance of about 1-1.5 mm. Preferably the surface extends transversely on each side of the rod path, with the air stream directing means on one side and the monitoring means on the other side of the path. The monitoring means, in particular, is preferably well spaced from the rod path (e.g. 10 mm or more).

BRIEF DESCRIPTION OF THE DRAWINGS

The invention will be further described, by way of example only, with reference to the accompanying diagrammatic drawing, which is a longitudinal sectional view of a cigarette rod monitoring device.

DESCRIPTION OF THE PREFERRED EMBODIMENT

The device 10 is located adjacent the path of a cigarette rod 12 in a cigarette making machine, just upstream of the cut-off and within the housing surrounding it.

The device 10 comprises a mounting block 14 having a slotted aperture 16 and a threaded bore 18 allowing vertically-adjustable connection of the device to a fixed part 20 of the machine (e.g. part of the cut-off housing). A monitoring block 22, which is of generally rectangular cross-section (i.e. perpendicular to the plane of the drawing), is connected below and extends outwards from the mounting block 14. The block 22 has an upper recess 24 which, together with a cover plate 26 and a lower part of the mounting block 14, defines a rectangular upper chamber 28. The block 22 has a lower blind bore 30 extending from its inner face 32 and terminating in a reduced diameter portion 34. A further bore 36 extends between a seat 38 adjacent the outer end of the chamber 28 and the lower face 40 of the block 22. This bore 36 intersects and connects with the bore 34.

A jet block 42 is connected to the inner part of the face 40. The upper face of the block 42 has a recess which forms with the face 40 a rectangular slot (or slit or passage) 44. The inner end of the slot 44 communicates with bores 46 and 48 in block 42, the bore 48 containing a threaded supply tube 50. The block 22 has a small diameter bore 52 which connects the bores 30 and 46.

The chamber 28 contains a microphone 54 located adjacent seat 38 and arranged to detect sound through the bore 36. The microphone 54 has a lead 56 connected to a signal lead 58 of a cable 60 by a connector 62 in the chamber 28. The end of the cable 60 is secured by a gland mounting 64 which also covers and seals the end of the bore 30.

The recess 28 contains light foam plastic packing (not shown) to aid location of the microphone 54, leads 56, 58 and connector 62. The bore 30 contains a cylindrical portion 66 of porous fibrous material (e.g. unwrapped cigarette filter rod).

In operation the position of the mounting block 14 is adjusted so that the lower flat face 40 of the monitoring block 22 is at the appropriate distance above the path of a cigarette rod 12. Typically the distance between the uppermost part of the cigarette rod 12 and the face 40 is about 1-1.5 mm.

An air supply line is connected to tube 50 of jet block 42 so that the pressure in the bore 46 is maintained at about 350 mb. Air exhausting through the slot 44 forms a stream which, due at least in part to Coanda effect, tends to maintain contact with the face 40. In passing the lower end of the bore 36 this air stream causes a characteristic sound to be detected by the microphone 54.

If the cigarette rod 12 has an open or otherwise imperfect seam, so that part of the wrapper extends upwardly towards the face 40, this will disturb the air flow adjacent the face and the sound detected by the microphone 54 will be measurably different for the duration of the disturbance.

When the air stream is disturbed by an open or damaged seam so that the microphone 54 detects a change in sound this may be arranged to cause a corresponding change in an analogue voltage signal in a circuit connected to the microphone. The circuit may be arranged to generate a fault signal only when a predetermined voltage change has occurred for a predetermined period, so as to avoid generation of incorrect fault signals due to noise peaks.

The signals received by the microphone could be processed in a similar way to processing of the signals received by the microphone in the arrangement of said U.S. Pat. No. 4685472.

As a typical microphone output signal is likely to vary with time (over relatively long periods) it is preferable to incorporate in the processing circuitry a form of signal conditioning including threshold adjustment. One way of achieving this is to assume that the frequency of fault signals is relatively low, so that the average signal over an appropriate sampling period, which period is long in relation to the duration of fault signals but short in relation to drift or variance of the typical output signal with time, may be regarded as corresponding to a no-fault condition. Hence the circuitry can be arranged to indicate a fault condition when the microphone output signal deviates from the average signal by a predetermined amount (which amount may itself be a function of the average signal).

If necessary, the cable 60 could include several separate leads, including a power lead for use, for example, where the microphone unit incorporates its own amplifier.

The slot 44 and bore 36 are further away from the cigarette rod 12 than analogous parts in the arrangement of said U.S. Pat. No. 4685475 and are less prone to blockage and/or contamination by tobacco dust or particles. In order to reduce further the possibility of contamination of the bore 36 through which the microphone 54 receives sound, the bore 36 is subjected to positive air pressure which causes a slight outward air flow for discouraging and/or removing contamination before it causes any problem. Air under pressure is bled to the bore 36 by way of bore 52, which forms a metering orifice 52 and which communicates with the bore 46 in jet block 42, and the bore 32 in monitoring block 22. The material 66 in bore 32 allows adequate air flow to reach the bore 36, via bore 34, while insulating the microphone 54 from sound caused by air flow through the bore 52. Although the air supplied by way of tube 50 should not contain dust or other contaminants the material 66 provides an effective filter for such contaminants. If necessary, in order to protect the slot 44 and bore 52 from possible eventual blockage by contaminants, a filter may be provided in the tube 50: conveniently this may comprise a rod-like portion of cigarette filter material.

Typical dimensions of the device 10 are:

| | |
|---|---|
| Cross-section of slot 44 | 5 mm × 0.5 mm |
| Length of slot 44 | 18 mm |
| Diameter of bore 36 | 3 mm |

-continued

| | |
|---|---|
| Length of bore 36 | 12 mm |
| Diameter of bore 30 | 7.5 mm |
| Length of bore 30 | 52 mm |
| Length of surface 40 beyond slot 44 | 50 mm |
| Width of surface 40 | 18 mm |
| Diameter of bore 52 | 0.55 mm–0.6 mm |

It may be noted that the width of the slot 44 is 5 mm. The air flow along the surface 40 has a corresponding width. The width of the surface 40 is 18 mm, however. In certain circumstances this has led to a build up of dust or other contaminants on the surface 40 at the edge of or beyond the normal path of the air flow, i.e. outside a central portion about 5 mm wide. In order to reduce or eliminate this build up, which may eventually interfere with the air flow to an extent which would possibly reduce accuracy or efficiency of the apparatus, it may be desirable to chamfer or otherwise recess the surface 40 other than in the region of the air flow from slot 44. The level of recessed surfaces 68 on each side of the surface 40 is indicated in the drawing.

During start up of a cigarette making machine it is often the case that the longitudinal seam of the wrapper is not well sealed and part of the wrapper can therefore run in contact with the surface 40 for significant periods. This, together with other occasional contact with the wrapper, can, over an extended period of use of the machine, create wear of the surface 40 which can affect accuracy and/or efficiency of the apparatus. It is therefore preferred that the surface 40 (or at least that part of it which may be contacted by wrapper material) should have a wear-resistant finish, e.g. by being anodised.

We claim:

1. A monitoring device, particularly for detecting imperfect longitudinal seams in the wrapper of a cigarette or cigarette filter rod, comprising a flat fixed surface which may be located adjacent to an axial path of the rod, means for directing an air stream along said flat fixed surface in a direction generally transverse to said path, and means for monitoring sound caused by said stream after it has passed adjacent said path, whereby disturbance of said stream caused by defects in a rod on said path may be detected by said monitoring means.

2. A device as claimed in claim 1, wherein the directing means and the flat fixed surface are arranged so that air flows in Coanda effect contact with said surface.

3. A device as claimed in claim 1, wherein the directing means comprises an air outlet, part of which is defined by said flat fixed surface.

4. A device as claimed in claim 1, wherein the sound monitoring means comprises a microphone located to receive sound through a passage having an opening in said flat fixed surface.

5. A device as claimed in claim 1, wherein said surface extends from one side of said rod path to the other side, said air directing means being on said one side, and said sound monitoring means comprising means communicating with said surface on said other side.

6. A device as claimed in claim 5, wherein said surface is part of a body housing said sound monitoring means.

7. A device as claimed in claim 6, wherein said body includes passage means admitting sound to said sound monitoring means.

8. A device as claimed in claim 7, wherein said body includes further passage means for passing air through said passage means to purge it of contaminants.

9. A device as claimed in claim 5, wherein said air directing means comprises a narrow rectangular slot for directing air parallel to said surface, and wherein said surface has a width corresponding to the width of said slot.

10. A device as claimed in claim 9, wherein said slot is partly defined by said flat fixed surface.

11. A monitoring device, particularly for detecting imperfect longitudinal seams in the wrapper of a cigarette or cigarette filter rod, comprising a fixed surface which may be located adjacent to an axial path of the rod, means for directing an air stream along said surface in a direction generally transverse to said path, and means for monitoring sound caused by said stream after it has passed adjacent said path, whereby disturbance of said stream caused by defects in a rod on said path may be detected by said monitoring means, said sound monitoring means comprising a microphone located to receive sound through a passage having an opening in said surface, and further including means for establishing an air flow in said passage to eliminate or reduce contamination.

12. A device as claimed in claim 11, including means for insulating the microphone from sound caused in generating said air flow in said passage.

13. A device as claimed in claim 12, wherein said insulating means comprises porous material through which air passes in response to said establishing means.

14. A device as claimed in claim 11, including a common air pressure source for said directing means and said establishing means.

* * * * *